United States Patent
Kondo et al.

(10) Patent No.: US 6,287,852 B1
(45) Date of Patent: Sep. 11, 2001

(54) PHOTOSYNTHETIC CULTURE APPARATUS AND GROUP OF PHOTOSYNTHESIS CULTURE APPARATUSES

(75) Inventors: Jiro Kondo, Tokyo; Yoshihisa Nakano, Sakai; Kazutaka Miyatake, Izumi; Nobuo Honami, Kawachinagano; Kenji Kanai, Neyagawa; Masahiko Tatsumi, Ibaraki, all of (JP)

(73) Assignee: Matsushita Electric Industrial Co., Ltd., Osaka (JP)

( * ) Notice: Subject to any disclaimer, the term of this patent is extended or adjusted under 35 U.S.C. 154(b) by 0 days.

(21) Appl. No.: 09/331,331
(22) PCT Filed: Oct. 12, 1998
(86) PCT No.: PCT/JP98/04575
§ 371 Date: Jun. 17, 1999
§ 102(e) Date: Jun. 17, 1999
(87) PCT Pub. No.: WO99/20738
PCT Pub. Date: Apr. 29, 1999

(30) Foreign Application Priority Data

Oct. 17, 1997 (JP) .................................................. 9-285525

(51) Int. Cl.[7] ..................................................... C12M 1/42
(52) U.S. Cl. .................................... 435/292.1; 435/294.1; 47/1.4
(58) Field of Search ............................. 435/292.1, 294.1, 435/257.1, 257.3; 47/1.4; 362/31

(56) References Cited

U.S. PATENT DOCUMENTS 4,555,864  12/1985  Mori .
5,233,679  * 8/1993  Oyama .

FOREIGN PATENT DOCUMENTS

| 57-102181 | * 6/1982 | (JP) . |
| 60-6189   | 1/1985   | (JP) . |
| 63-103296 | 7/1988   | (JP) . |
| 3-9306    | 1/1991   | (JP) . |
| 04-166017 | * 6/1992 | (JP) . |
| 5-34687   | 2/1993   | (JP) . |
| 5-153957  | 6/1993   | (JP) . |
| 05-244932 | * 9/1993 | (JP) . |
| 6-69903   | 9/1994   | (JP) . |
| 6-317796  | 11/1994  | (JP) . |
| 08-009809 | * 1/1996 | (JP) . |
| 9-23874   | 1/1997   | (JP) . |

OTHER PUBLICATIONS

Japanese language search report for Int'l Appln No. PCT/P98/04575 dated Feb. 22, 1999.

English translation of Form PCT/ISA/210. Feb. 22, 1999.

* cited by examiner

Primary Examiner—William H. Beisner
(74) Attorney, Agent, or Firm—Ratner & Prestia

(57) ABSTRACT

A photosynthetic culture system has a culture bath holding an fluid containing plant microorganisms, carbon dioxide supplying means for supplying carbon dioxide to the fluid in the culture bath, light-conducting plate in the form of a flat plate placed oppositely to a light-receiving culture surface existing on the side of said culture bath, and light-receiving panel mounted on the upper end surface of the light-conducting plate. Further said light-conducting plate has the function of turning incident light from said light-receiving panel by right angles to conduct the light uniformly to said light-receiving culture surface of said culture bath.

19 Claims, 8 Drawing Sheets

1 6 Photosynthetic Culture System

1 Plant Microrganisms
3 Culture Bath
4 Light-Receiving Culture Surface
5 Carbon Dioxide-Supplying Means
8 Light-Conducting Plate
10 Light-Diffusing Surface
12 Light-Converging Portion
13 External Light-Receiving Surface
14 Sunlight
15 Diffused Light 16 Photosynthetic Culture System 17  Connecting Pipe for Supplying Fluid
18  Connecting Pipe for Transferring Product
19  Connecting Pipe for Supplying Carbon Dioxide (Efficiency of introducing light from 24 to 15 is 90% or more.)

3 : Culture Bath
8 : Light-Conducting Plate
14 : Sunlight
15 : Diffused Light
21 : Supporting Portion
22 : Condenser
24 : Input Light 3 : Culture Bath
8 : Light-Conducting Plate
22 : Condenser 31 : Semicylindrical Lens 3 : Culture Bath
8 : Light-Conducting Plate
32 : Integrated Lens

PHOTOSYNTHETIC CULTURE APPARATUS AND GROUP OF PHOTOSYNTHESIS CULTURE APPARATUSES

THIS APPLICATION IS A U.S. NATIONAL PHASE APPLICATION OF PCT INTERNATIONAL APPLICATION PCT/JP98/04575.

TECHNICAL FIELD

This invention relates to a photosynthetic culture system which fixes carbon dioxide by photosynthetically culturing and growing algae, plant microorganisms or the like.

BACKGROUND ART

Fossil fuels such as coal, oil and natural gas recently used in thermal power plants etc. release a vast amount of carbon dioxide into the atmosphere by burning. Increase of the released carbon dioxide in the atmosphere will deteriorate global environment by causing global warming etc., in addition, it will significantly affect the human society through the occurrence of natural disaster and heavy damage of crops, because increase of carbon dioxide in the atmosphere is the cause of a frequent drought, heavy rain and floods.

Thus, the development of the technology has been long-awaited which can fix carbon dioxide with less energy to decrease the amount of carbon dioxide released into the atmosphere. And as a simple, safe and effective method, a method has been investigated and is about to be utilized to fix carbon dioxide in the atmosphere using photosynthesis of plant microorganisms which is caused by irradiation of sunlight etc. However, in the construction of the conventional photosynthetic culture systems using plant microorganisms, since their culture baths need to ensure a certain volume of fluid, after photosynthesis proceeds to some extent, light required for photosynthesis does not reach the whole solution sufficiently. Therefore, methods have been used to make photosynthetic culture baths shallow or stir the fluid in the bath so that light will reach the whole solution.

For example, the amount of carbon dioxide in burning gas released from thermal power plants is as vast as about 5000 t/day at 500000 kW output power of burning natural gas, and when burning coal or oil, carbon dioxide emission will be further increased. In such a situation, in order to fix carbon dioxide released from thermal power plants, the systems which are as compact as possible and need less energy for the fixation are desirable. In order to solve these problems, improvements are required in the carbon dioxide fixing technology which are now in use globally such as enhancement of the carbon dioxide fixing ability of photosynthetic culture baths and systems including an optical system, enhancement of efficiency, increase of controllability of the products of photosynthetic reaction.

However, in view of the fact that an effective depth of the culture bath for photosynthesis is only several cm, one of the above methods, in which photosynthetic culture baths are made shallow, has a problem that the area of the photosynthetic culture systems must be extremely large-scale in order to ensure sufficient volume of culture solution. And the other method, in which the fluid is stirred, has also a problem that the whole culture bath is not made good use of since the fluid always subjected to photosynthesis is restricted within the limits where light can reach.

Further, in the conventional photosynthetic culture baths utilizing natural sunlight, since the surface of the solution which is a light-receiving surface is irradiated with an intensive sunlight, light intensity more than needed is wasted and it causes some troubles. In addition, with the progress of photosynthesis, the number of the cells is increased, which prevents light from reaching the depths of the fluid.

DISCLOSURE OF THE INVENTION

In light of these problems of the prior art, the purpose of the present invention is to provide a photosynthetic culture system and a collective photosynthetic culture system which allow to control the waste of optical energy, to make good use of the whole culture bath, and to control the increase of their installation area even when ensuring a sufficient volume of culture solution.

In order to cope with the foregoing problems and subjects, the present applicants propose the present invention, based on the basic and scientific study on photosynthetic media, the discovery of the photosynthetic media having good carbon dioxide fixing ability, a good knowledge of operation in a thermal power plant and a deep knowledge of carbon dioxide emission and its fixation, which will realize the introduction of photosynthetic media having the good carbon dioxide fixing ability as well as the introduction of the optimum environment to promote efficiency of photosynthesis and has the features described below.

The photosynthetic medium used in the present invention is, for example, Euglena gracilis which are plant microorganisms.

With the progress of photosynthesis, the number of the photosynthesized cells is increased, which prevents light from reaching the depths of the fluid. Therefore, the thickness of the culture solution is decreased in the direction in which light travels. In addition, in order to eliminate the waste of energy due to an excess of the natural sunlight irradiation over the required amount, the area of the natural sunlight-receiving surface is effectively expanded and the light is conducted to the light-receiving culture surface via the natural sunlight-receiving surface. The natural sunlight-receiving surface and the light-receiving culture surface are arranged to have a rectangular relationship.

The present invention according to one aspect is a photosynthetic culture system comprising: a culture bath holding an fluid containing plant microorganisms, carbon dioxide supplying means for supplying carbon dioxide to the fluid in the culture bath, light-conducting means in the form of a flat plate placed oppositely to a light-receiving culture surface existing on the side of the culture bath, and light-receiving means mounted on the upper end surface of the light-conducting means, wherein the light-conducting means has the function of turning the incident light from the light-receiving means by substantially right angles to conduct the light uniformly to the light-receiving culture surface of the culture bath.

The present invention according to another aspect is a collective photosynthetic culture system, wherein more than one photosynthetic culture system according to are arranged so that the light-receiving culture surfaces of said culture baths will be in parallel to one another and the photosynthetic culture systems are connected to one another with a connecting pipe for supplying an fluid, a connecting pipe for transferring products, and a connecting pipe for supplying carbon dioxide.

DESCRIPTION OF SYMBOLS

1 Plant Microrganisms
3 Culture Bath
4 light-Receiving Culture Surface
5 Carbon Dioxide-Supplying Means
8 Light-conducting Plate
10 Light-Diffusing Surface
12 Light-Converging Portion
13 External Light-Receiving Surface
16 Photosynthetic Culture System
17 Connecting Pipe for Supplying Fluid
18 Connecting Pipe for Transferring Product
19 Connecting Pipe for Supplying Carbon Dioxide
22 Condenser
31 Semicylindrical Lens
32 Integrated Lens

BEST MODE OF THE EMBODIMENTS

Referring now to the embodiments of the present invention with reference to the accompanying drawings.

Embodiment 1

Figure 1:
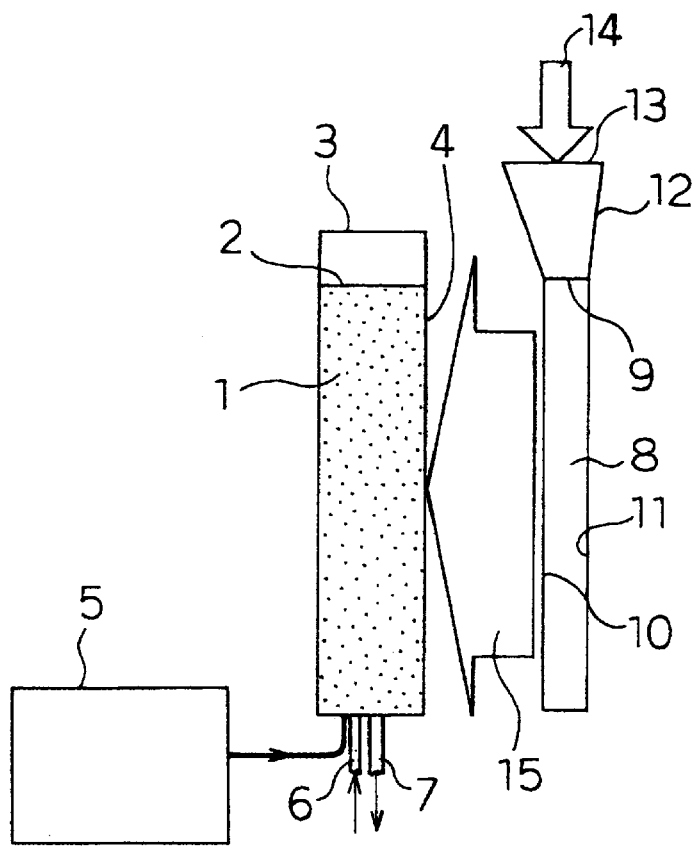
FIG. 1 is a diagram illustrating the construction of one example of a photosynthetic culture system made pursuant to Embodiment 1 of the present invention.

FIG. 1 is a diagram illustrating the construction of one example of a photosynthetic culture system made pursuant to Embodiment 1 of the present invention. Specifically, the photosynthetic culture system made pursuant to Embodiment 1 of the present invention basically comprises: a culture bath 3 which holds an fluid 2 containing plant microorganisms 1 and whose side consists of a light-receiving culture surface 4; carbon dioxide-supplying means 5 which supplies carbon dioxide to the fluid 2 in the culture bath 3; a light-conducting plate 8 in the form of a flat plate (or a light-conducting cavity), as light-conducting means, which has a light-converging portion 12, as light-receiving means, having on its top a flat external light-receiving surface 13 receiving light 14 from outside and which has a light-intake 9 for taking in the light converged in the light-converging portion 12 and which turns the incident light nearly right angles and reflects the light 15 to the light-receiving culture surface 4 of the above culture bath 3. Here, one of the surfaces of the light-conducting plate 8, which is on the side of the culture bath 3, consists of a diffusing surface 10 provided with, for example, a light-diffusing sheet which diffuses light, and the other surface is provided with a diffused reflection layer 11. And the culture bath 3 is connected to an fluid-supplying pipe 6 for supplying an fluid and a product-taking pipe 7 for taking products. Materials for the light-converging portion may be those having a high light transmittancy, such as acrylic and glass, and they can be selected in terms of cost, performance, machinability etc.

In the above construction, external light 14 enters through the external light-receiving surface 13 and is converged in the light-converging portion 12, and the converged light enters through the light-intake 9 of the light-conducting plate 8. The light having entered the light-conducting plate 8 is subjected to diffused reflection on the diffused reflection layer 11 and also subjected to diffusion on the diffusing surface 10 before being transmitted to the whole light-conducting plate 8, and almost completely uniformed light is conducted from the diffusing surface 10 of the light-conducting plate 8 to the whole light-receiving culture surface 4 of the culture bath 3.

To a light-conducting plate 8 described above, a back light technology used in a liquid crystal display can be applied. In a liquid crystal back light, for example, the upper end portion of a transparent acrylic board having almost the same shape as the screen of the display serves as a light-receiving portion, and in order for the back of the acrylic board to function as a diffused reflecting plane, small disks of translucent film of which diameter and space are devised are arranged on the entire back portion by means of the printing process or the like and a sheet of white paper is pasted on that portion. Further, a sheet of the same white paper as above is also pasted on the both side portions and lower end portion of the transparent acrylic board, and on the surface of the white paper a light-diffusing sheet is pasted in order to obtain a uniform brightness on the screen (for example, applicable is technology described in Japanese Patent Application Laid-Open No. 3-9306, Japanese Patent Application Laid-Open No. 6-317796, Japanese Utility Model Application Laid-Open No. 6-69903, and Japanese Patent Application Laid-Open No. 5-34687). As described above, a back light used in a liquid crystal display may be applied to the light-conducting plate 8 of the present invention; however, uniformity of light which a liquid crystal back light requires is not required for the light-conducting means of the present invention. And as for a light-diffusing sheet, since it absorbs light, it is more advisable to use a light-conducting plate without a light-diffusing sheet to avoid loss of efficiency.

Experimentally, the efficiency of diffusing and transmitting the incident light from one end of the light-conducting plate to the whole surface of the light-conducting plate is about 90%. Photosynthesis was performed using natural sunlight in the culture bath of the present invention utilizing the above technology. The relationships to energy will be discussed below.

On the basis of the quantum theory, at the wave length of 680 nm which is optimum for photosynthesis, the number of photons per 1 kWh is: 1 kWh=$1.2 \times 10^{26}$ photons, and 1 mol×photon=0.17 MJ. Based on the theoretical limit of photosynthesis, 1 molecular of $CO_2$ is fixed by 8 photons and energy required for fixing 1 molecular of $CO_2$ is: 8 mol×photon=0.38 kWh=1.36 MJ, while the maximum of the experimental results of photosynthesis is, for example, 9 mol×photon=0.43 kWh=1.53 MJ.

As for solar energy, the average incident solar energy in the latitude of Japan is 1 kW/m²; and if solar radiation lasts 4 hours a day, the energy will become: 4 kWh/m² ·day=14 MJ/m²·day. From this, $CO_2$ fixing ability is: 4 kWh/m² ·day/0.43 kWh/0.044 (kg—$CO_2$)=0.41 (kg—$CO_2$/m² ·day)= 0.1 (kg—$CO_2$/kWh ·day), when using the maximum of the experimental results of photosynthesis.

In the case of an LNG power plant, if the plant operates 24 hours a day, the generated energy per day is: $1.2 \times 10^7$ kWh/day, and at the same time $CO_2$ emission per day is 5000 (t—$CO_2$/day); however, in actuality, $CO_2$ emission per day is below 3200 (t—$CO_2$/day) (about 64%) considering working factor etc.

On the basis of the data so far, the area required for $CO_2$ fixation is: 3200 (t—$CO_2$/day)/0.41 (kg—$CO_2$/m² ·day)=$8 \times 10^6$ m² =800 ha. And solar energy received by the area of 800 ha becomes $3.2 \times 10^7$ kWh/day, about 3 to 4 times as much as the generated energy, which is a reasonable value in terms of theoretical energy balance of photosynthesis.

In the above illustration of FIG. 1, the light-conducting plate 8 and the culture bath 3 are spaced. However, this photosynthetic culture system is more practically effective when more than one systems are arranged in a collective manner. Therefore, a photosynthetic culture system is constructed so that the light-diffusing surface of the light-conducting plate 8 will be in contact with the light-receiving culture surface of the culture bath 3. Alternatively, this type of photosynthetic culture system may be constructed so that the side wall of the culture bath 3 forming a light-receiving culture surface will also serve as a light-conducting plate 8. As for the external light-receiving surface 13 of the light-converging portion 12, its shape and size are the same as those of the synthesis of the top surfaces of both the culture bath 3 and the light-conducting plate 8 existing under it.

Figure 2:
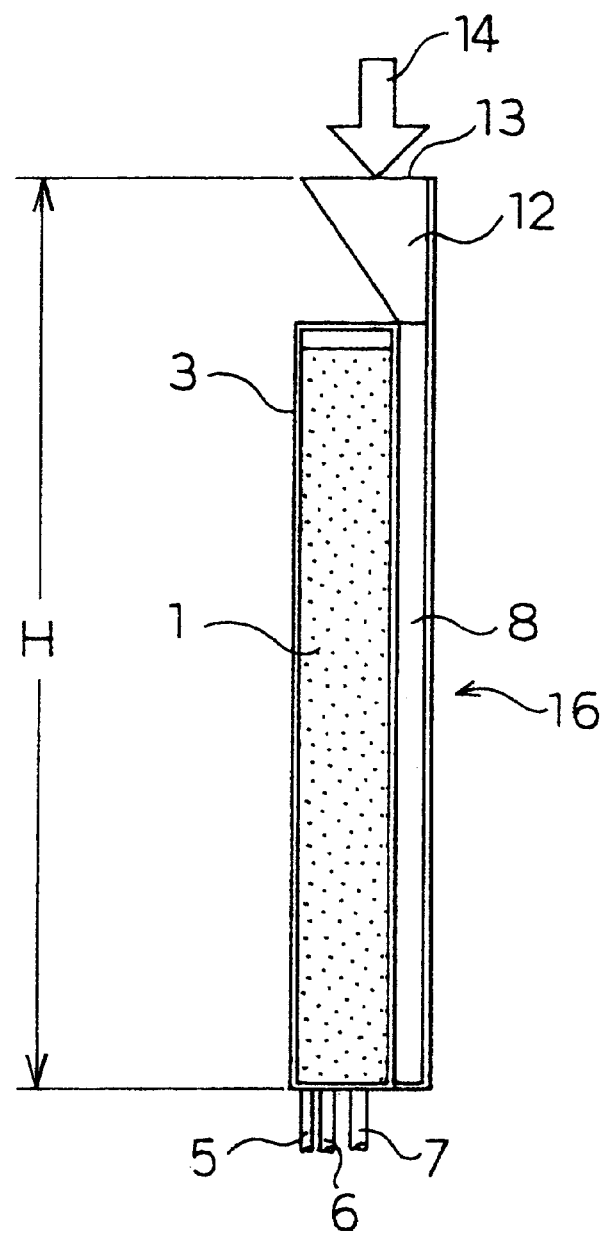
FIG. 2 is a diagram illustrating the construction of another example of a photosynthetic culture system made pursuant to Embodiment 1 of the present invention.
Figure 3:
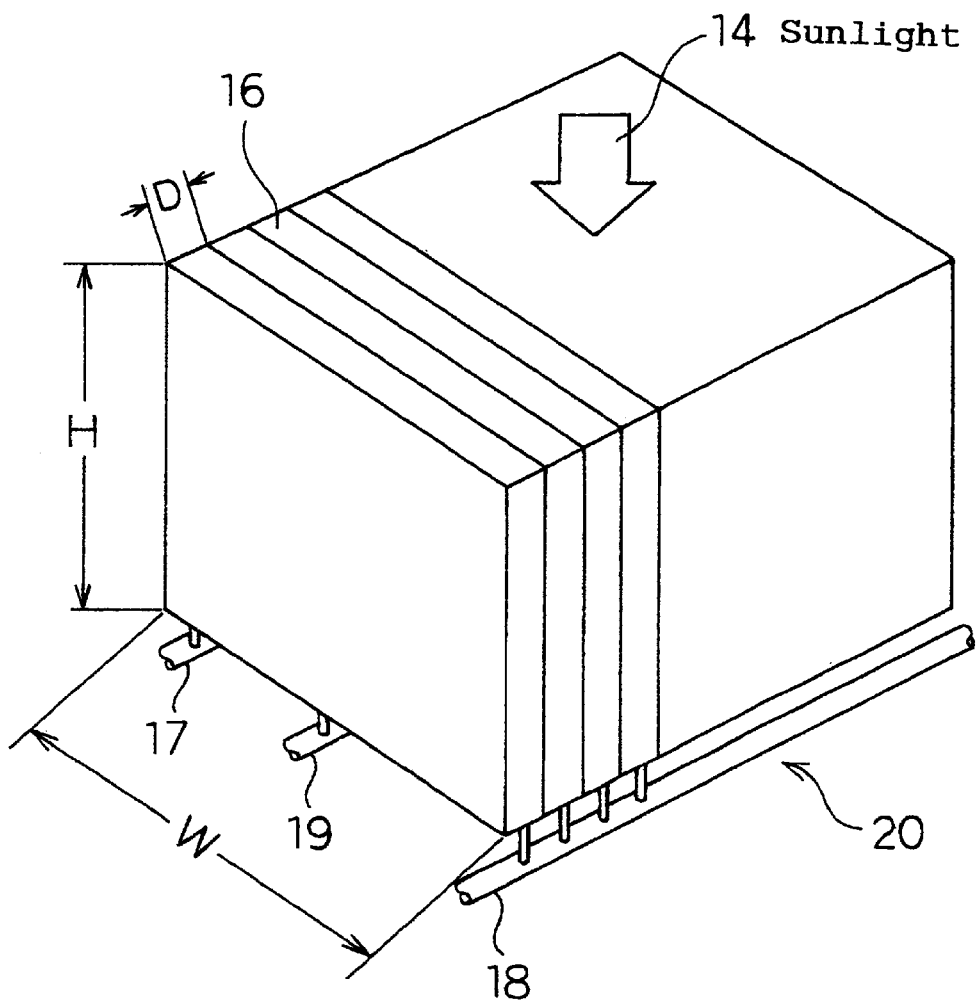
FIG. 3 is a schematic diagram illustrating the construction of a collective photosynthetic culture system made up by laminating more than one photosynthetic culture system, as a unit, made pursuant to Embodiment 1 of the present invention.

FIG. 3 is a schematic diagram illustrating the construction of a collective photosynthetic culture system 20 in which more than one photosynthetic culture system 16, which is a unit culture bath of FIG. 2, are arranged in a laminated manner and the culture baths are connected to one another with a connecting pipe for supplying an fluid 17, a connecting pipe for transferring product 18 and a connecting pipe for supplying carbon dioxide 19. In FIG. 3, if the shape of the light-receiving culture surface 13 of a unit photosynthetic culture system 16 is rectangular and its long and short sides are W and D, respectively, the width of the external light-receiving surface of the culture bath 3 is allowed to correspond to W and the sum of the thickness of the culture bath and that of the light-conducting plate 8 is allowed to correspond to D (see FIG. 2). Accordingly, the shape and size of the external light-receiving surface of the whole collective photosynthetic culture system 20 are the same as those of the top surface of the laminated culture baths and light-conducting plates under the external light-receiving surface, which allow light from outside to enter effectively. Construction of a collective photosynthetic culture system by laminating the required number of unit photosynthetic culture systems of the present embodiment in the transverse direction makes it possible to increase performance capacity of the system while keeping its energy balance.

In cases where plant microorganisms supplied to the culture bath are, for example, Euglena gracilis, when the number of cells in the culture bath reaches of the order of 1 million per 1 ml, the light transmission distance is decreased to about 1 cm. This means that the volumetric efficiency is good when the thickness of the culture is about 1 to 5 cm.

As a highly efficient culture bath using natural sunlight, the area of the light-receiving culture surface is, for example, set at a value about 10 times as large as that of the external light-receiving surface. When the external light-receiving surface is irradiated with the maximum illumination of about 120000 luces of the sunlight, it diffuses the sunlight and the light-receiving culture surface is irradiated with about 3000 to 10000 luces (70–200 $\mu$mol/m²/s) which is suitable for cultivating plant microorganisms (Euglena gracilis). Thus optical energy can be effectively utilized.

When the thickness D of the unit photosynthetic culture system in this example is set at about 3 cm and the height H of the same is set at 30 cm to 1 m, the calculated value of the carbon dioxide fixing ability of 0.2–0.5 kg/m³ is obtained. On the other hand, for conventional culture baths without a light-conducting means, the carbon dioxide fixing ability per unit volume may be capable of being decreased since too intensive light inhibits photosynthesis and light cannot be effectively used in the depths of such baths. Consequently, it is expected that the culture baths using light-conducting means shown in the present embodiment has about 10 times as high volumetric efficiency as that of the culture baths without a light-conducting means to which light is irradiated only from above, even when they have the same shape and size.

When the height H of the photosynthetic culture system according to the present embodiment is set at 1 m, since the actual situation of carbon dioxide emission from a thermal power plant of 500000 kW power is of the order of 3200 t per day, the area of the system required for carbon dioxide fixation is about 800 ha.

Embodiment 2

Figure 4:
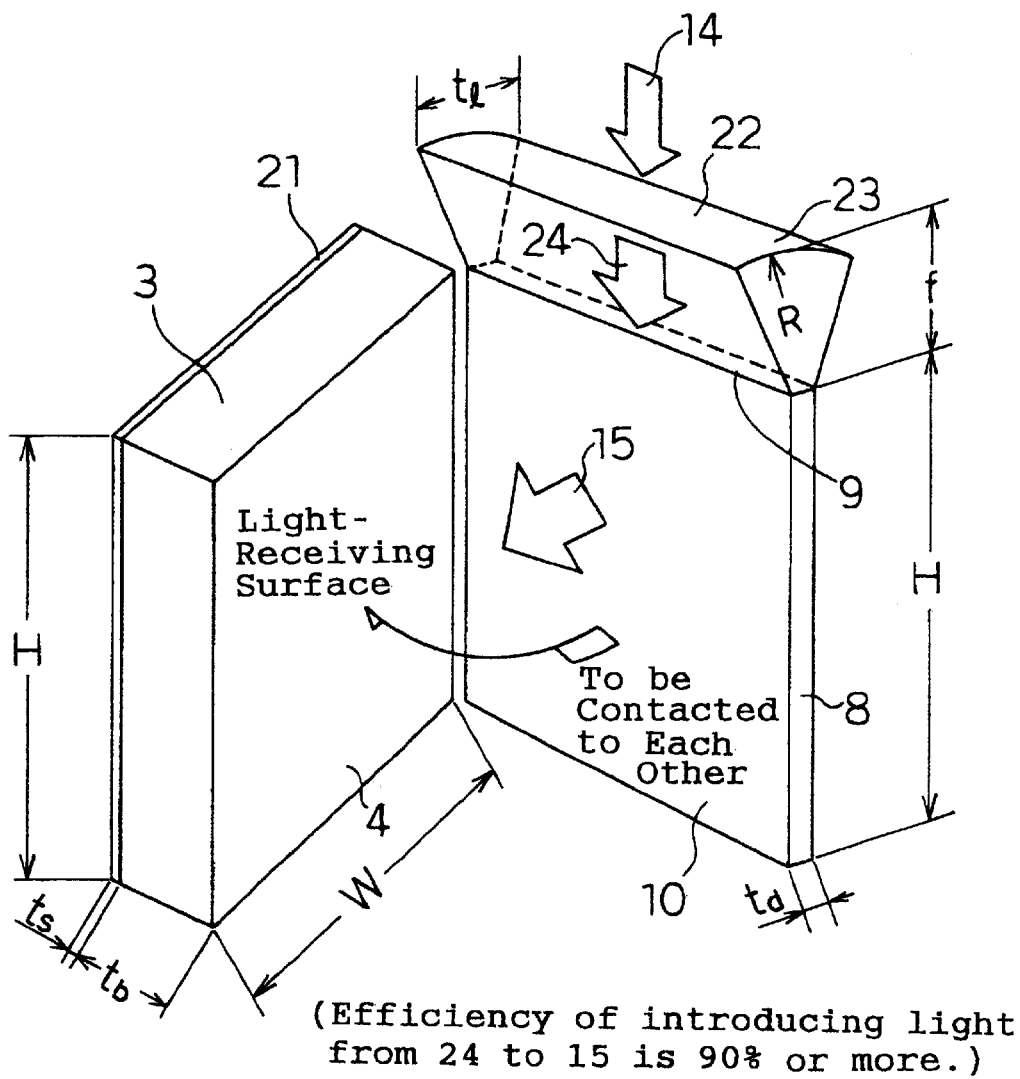
FIG. 4 is a diagram illustrating the construction of a culture bath and a light-conducting portion of a photosynthetic culture system made pursuant to Embodiment 2 of the present invention.

FIG. 4 is a diagram illustrating the construction of a culture bath and a light-conducting portion of a photosynthetic culture system made pursuant to Embodiment 2 of the present invention. Specifically, similar to the construction shown in FIGS. 1 and 2 described above, a photosynthetic culture system made pursuant to Embodiment 2 of the present invention basically comprises: a culture bath 3 which holds an fluid containing plant microorganisms and whose side consists of light-receiving culture surface 4; a condenser 22 as light-receiving means whose top has a convex external light-receiving surface 23 which receives external light 14; a light-conducting plate 8 in the form of a flat plate which turns incident light from the condenser 22 right angles and reflects light 15 to a light-receiving culture surface 4 of the above culture bath 3. In accordance with the foregoing embodiment 1, an external light-receiving surface of the light-converging portion is flat; however, in accordance with the present embodiment 2, a condenser 23 is used as an external light-receiving surface. And in accordance with the present embodiment 2, there is provided a supporting portion 21 on the surface opposite to the light-receiving culture surface 4 of the culture bath 3; however, if the side wall of the culture bath 3 is strong enough, the supporting portion may be unnecessary. Although not shown in FIG. 4, like the foregoing embodiment 1, carbon dioxide-supplying means, a connecting pipe for supplying an fluid and connecting pipe for transferring product are connected to the culture bath 3.

Figure 5A:
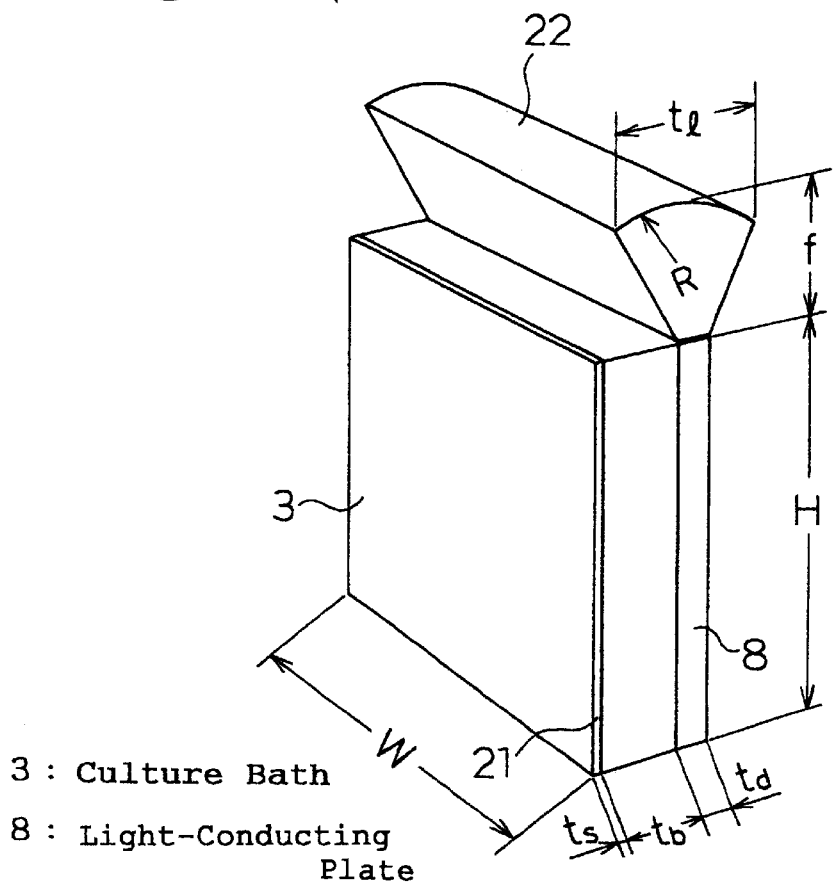
FIG. 5(a) is a diagram illustrating the construction of a photosynthetic culture system made pursuant to Embodiment 2 of the present invention.

In FIG. 4, td indicates the thickness of the light-conducting plate 8, tb the thickness of the culture bath 3, ts the thickness of the supporting portion 21, and tl the width of the condenser 22. W indicates the width of the culture bath 3 and it is almost the same as the width of the light-conducting plate 8 and the length of the condenser 22. H indicates the depth of the culture bath 3 and it is almost the same as the height of the light-conducting plate 8. f indicates the focal distance of the condenser 22 and R the radius of curvature of the convex surface of the same. In this case, the efficiency of introducing input light 24 which enters the light-conducting plate 8 to diffused light 15 is 90% or more. One example of a construction of this type photosynthetic culture system will be shown below. Light entering the light-receiving culture surface 4, that is, $$\text{Diffused light } 15 = \text{input light} 24 \times (td/H)$$
$$= \text{sunlight } 14 \times (tl/td) \times (td/H)$$
$$= \text{sunlight } 14 \times (tl/H)$$

and the width of the condenser tl=tb+ts+td=2r
When r=25 mm, the radius R=30 mm, the focal distance=50 mm,
R/r=1.2, f/r=2, and the width across corners of the light-diffusing surface=13"=275 mm×209 mm FIG. 5(a) illustrates a state in which the light-receiving culture surface 4 of the culture bath 3 and the light-diffusing surface 10 of the light-conducting plate 8 shown in FIG. 4 are closely touched to each other, and that is a state when they are actually used. In the construction shown in FIG. 5(a), the sunlight 14 outside enters through the external light-receiving surface 23 and is converged by the condenser 22, and the input light 24 enters the light-conducting plate 8 through the light intake 9. The light having entered the light-conducting plate 8 is transmitted to the whole light-conducting plate 8, and almost completely uniformed diffused light 15 is conducted from the light-diffusing surface 10 of the light-conducting plate 8 to the whole light-receiving culture surface 4 of the culture bath 3.

Figure 5B:
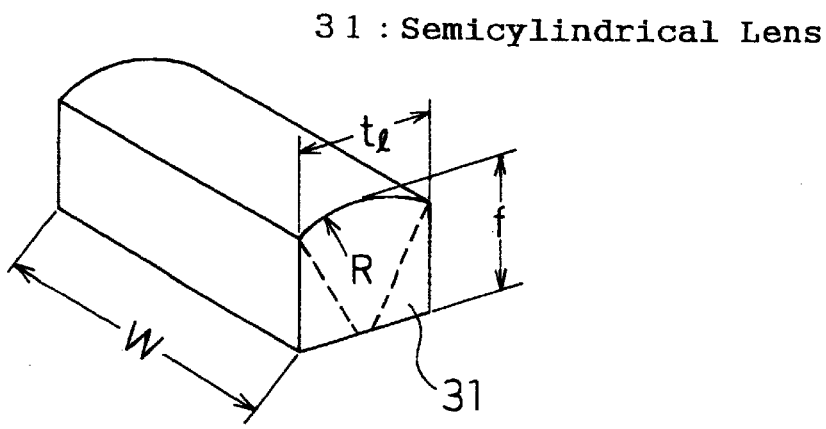
FIG. 5(b) is a diagram illustrating another example of a condenser.

In the present embodiment 2, this type of photosynthetic culture system may be constructed so that the side wall of the culture bath 3 forming a light-receiving culture surface 4 will also serve as a light-conducting plate 8. The photosynthetic culture system is constructed so that the shape and size of the projection surface of the external light-receiving surface 23 of the condenser 22 from above will be the same as the synthesis of the top surfaces of both the culture bath 3 and the light-conducting plate 8 which are under the external light-receiving surface 23. If the condenser 22 is a semicylindrical lens 31 shown in FIG. 5(b), not only it will bring the same good results, but also it will be very convenient when more than one lens are collectively arranged, since semicylindrical lenses are easy to manufacture and they can be installed to be closely touched to one another on their sides. In this case, though the lens differs from the condenser 22 shown in FIG. 5(a) in shape, it also condenses incident light from outside in the light-conducting plate like the condenser 22 shown in FIG. 5(a), as shown with dotted lines. Materials for the condenser may be those having a high light transmittance such as acrylic and glass, and they can be selected in terms of cost, performance, machinability etc.

Figure 6:
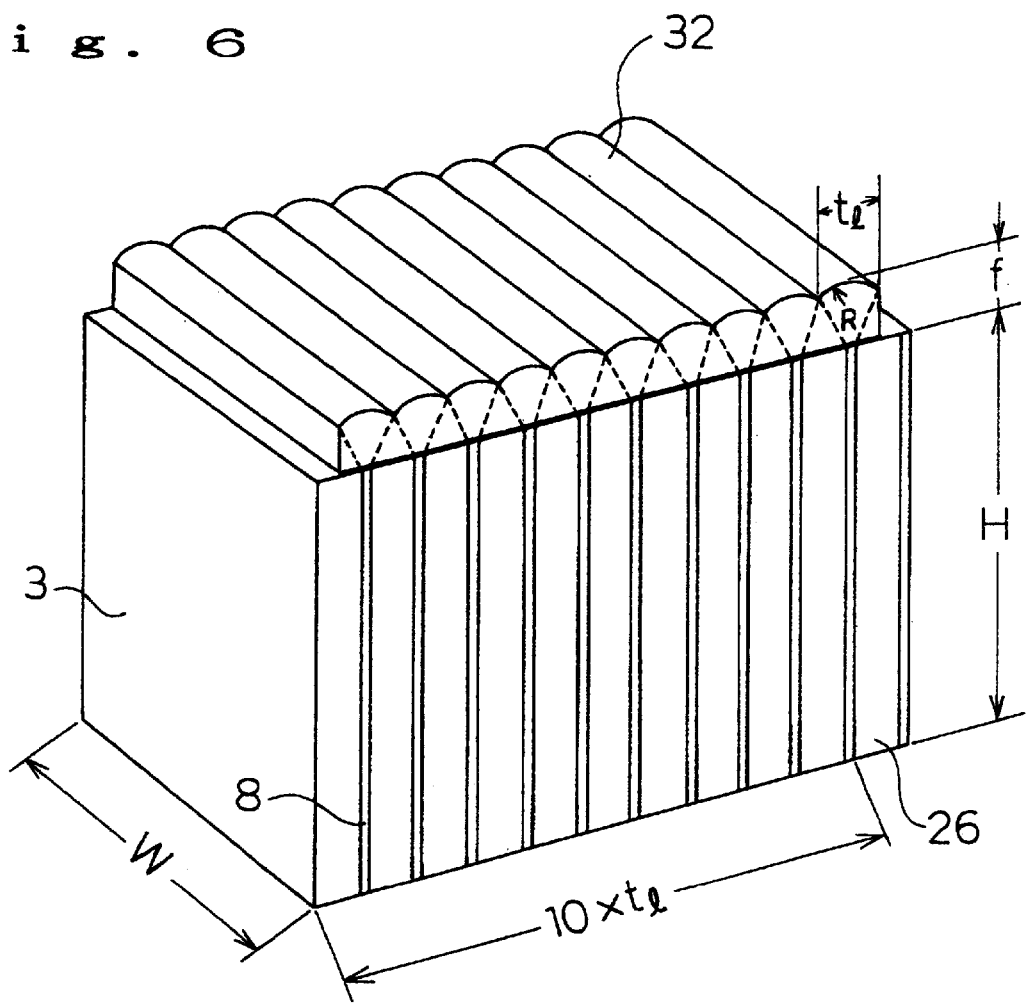
FIG. 6 is a diagram illustrating the construction of a collective photosynthetic culture system which is made up by laminating more than one photosynthetic culture system, as a unit, made pursuant to Embodiment 2 of the present invention.

FIG. 6 is a schematic diagram illustrating the construction of a collective photosynthetic culture system in which more than one photosynthetic culture system 26, as a unit, are arranged in a laminated manner and their culture baths are connected to one another with a connecting pipe for supplying fluid, a connecting pipe for transferring product and a connecting pipe for supplying carbon dioxide which are not shown in the figure. In the construction shown in FIG. 6, a supporting portion is omitted and, light-receiving means is made up of an integrated lens 32 which is integrally formed from semicylindrical lenses by pressing or the like. Such a construction allows to increase the output efficiency and reduce production cost. It goes without saying that light-receiving means may be made up by arranging more than one individual semicylindrical lenses 31 shown in FIG. 5(b) side by side.

In FIG. 6, if the area of the sunlight-receiving surface=the width of the condenser (tl)×the length of the condenser (W), the volume of the culture bath=the width of the condenser (tl)×the length of the condenser (W)×the height of the culture bath (H),
    the sunlight diffusivity=the height of the culture bath (H)/the width of the condenser (tl), and
    the illuminance of the surface of the culture bath=the illuminance of the surface vertical to sunlight/the sunlight diffusivity,
    the sunlight diffusivity is of the order of 12, provided that the required illuminance of the surface of the culture bath is 10000 luces (135 $\mu$mol/sm$^2$) and the average illuminance of the surface vertical to sunlight is 120000 luces. Accordingly, in the construction according to the present embodiment, if the thickness of the culture bath tb is almost equal to the width of the condenser tl and the thickness of the culture bath tb is 3–10 cm, the depth of the culture bath H is about 1 m at the most. This is true of the foregoing embodiment 1. Use of a culture bath deeper than 1 m leads to an insufficient supply of light, and even when light is conducted to the depths with optical fibers or the like, there remains a problem of energy balance.

As for a light-conducting plate 8, in cases where light is conducted from one end of the light-conducting plate only and the light is to be conducted to the whole diffusing surface uniformly, the size of the light-conducting plate is suitably 13"–17". When the depth is about 30 cm, it is suitably about 17"(41 cm×32 cm), wherein the thickness of the culture bath is calculated from the sunlight diffusivity to be about 3 cm.

The amount of fixed $CO_2$ will be described below.

The amount of energy taken in by a unit culture bath depends on the area of the light-receiving surface and is represented by 4tl·W (kWh). The amount of $CO_2$ fixed with this amount of energy is then represented by 0. 4tl·W (kg), wherein the depth of the culture bath H is optional as long as it is suitable for culture (provided the unit of tl and w is the m). Accordingly, when using n unit culture baths, the total amount of fixed $CO_2$ is 0. 4n·tl·W (kg).

In the above embodiments, the system of the present invention was all illustrated by taking the case where light irradiating the external light-receiving surface is natural sunlight; however, light is not limited to natural sunlight, but artificial light of high efficiency and luminance, for example, fluorescent light, LED and HID lamp may be used to irradiate the external light-receiving surface. In such a case, combination of artificial light with natural sunlight according to the weather, time, etc. makes more efficient carbon dioxide fixation by photosynthesis.

Figure 7:
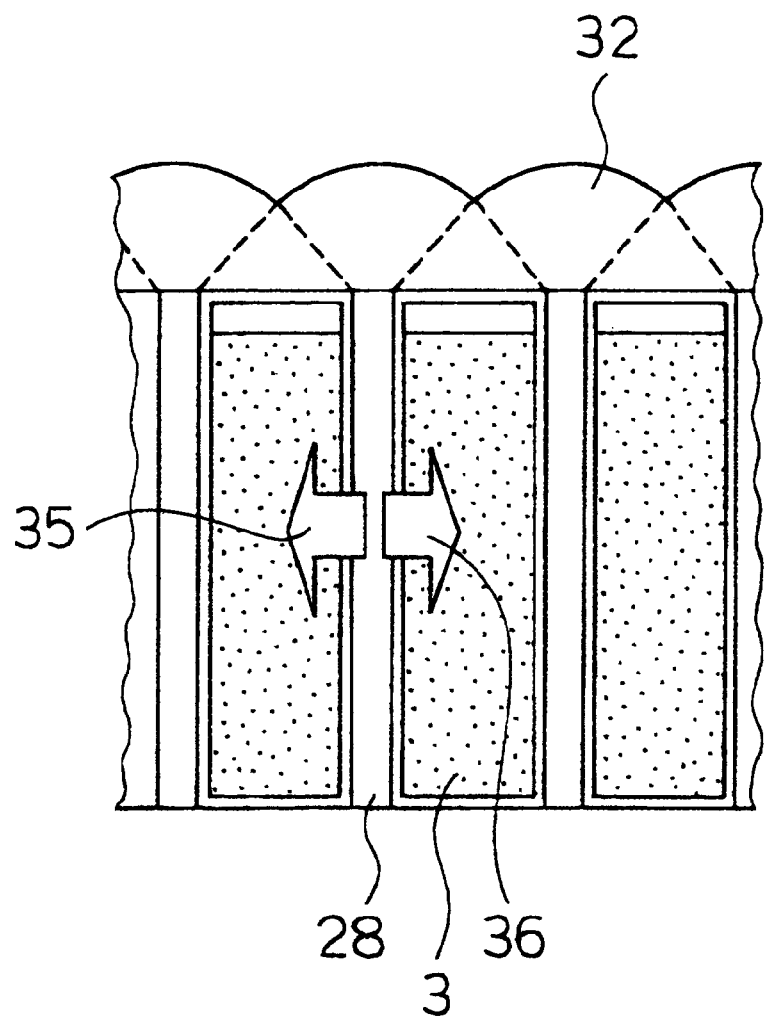
FIG. 7 is a diagram illustrating one example of a photosynthetic culture system of the present invention which uses a light-conducting plate in which incident light is diffused on both its surfaces.

Further, in the above embodiments, the system of the present invention was all illustrated to have the construction in which incident light is diffused and reflected to one surface of the light-conducting plate only; alternatively, the system of the present invention may have a construction in which, for example, as shown in FIG. 7, incident light is diffused and reflected to both surfaces of the light-conducting plate, that is, a construction in which a light-conducting plate 28 is used which is provided with a diffusion layer on both of the two surfaces opposite to each other and incident light is conducted to two culture baths 3 adjacent to the both surfaces. In such a case, since light enters a culture bath 3 from its both sides, it is possible to increase the thickness of the culture bath 3, which means that a collective photosynthetic culture system having the same volume can be made up of a decreased number of unit culture baths.

Further, in the above embodiments, the system of the present invention was all illustrated to have the construction in which the surface of the light-receiving means (the light-converging portion of Embodiment 1 and the condenser of Embodiment 2) is not subjected to surface treatment; however, the present invention is not limited to this, one surface or both surfaces of the light-receiving means may be subjected to protective coating with a thin film such as UV protective coat. This makes it possible to protect each part of the system from deterioration by UV and mechanical damage, in addition, this is effective in dust protection.

Figure 8:
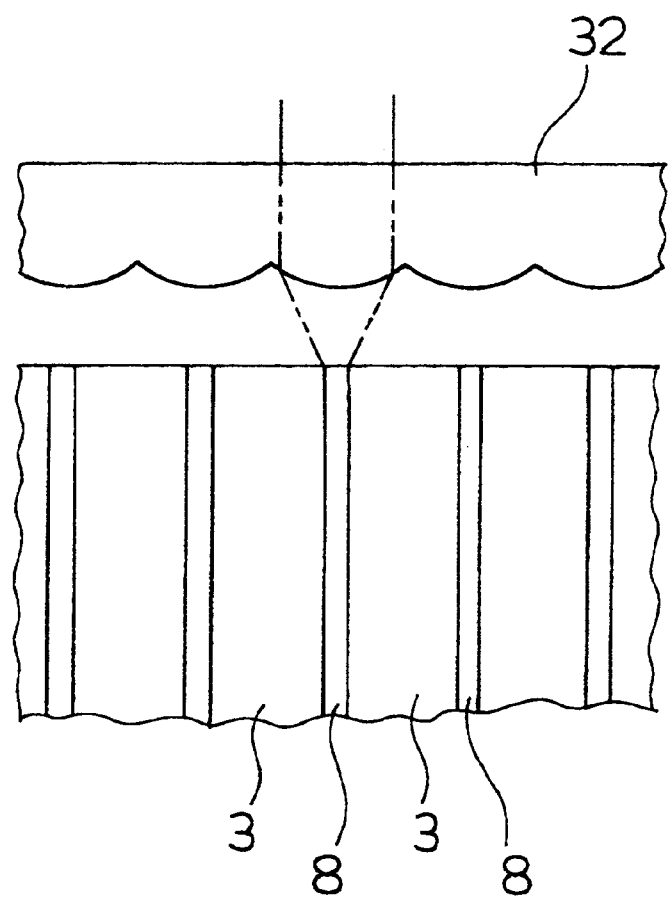
FIG. 8 is a diagram illustrating one example of a photosynthetic culture system of the present invention in which the convex surface of the condenser is turned downwardly.

In the above Embodiment 2, the system of the present invention was illustrated to have the construction in which the convex surface of the condenser is the external light-receiving surface; on the contrary, as shown in FIG. 8, the system of the present invention may have the construction in which the convex surface of the condenser is turned downwardly toward the light-conducting plate 8. In such a case, there arises a small gap between the condenser 32 and the light-conducting plate 8, however the size is too small to be a problem. This construction has the advantage such that, since the top surface is flat, dust is hard to accumulate and it is easy to clean. In FIG. 8, the system is constructed so that each light-conducting plate 8 serves as a side wall of each culture bath 3 adjacent to its right and its left. In such a case, only one side wall is required for the two adjacent culture baths 3, which makes the construction easier.

Further, in the above embodiments, the system of the present invention was all illustrated by taking the case where plant microorganisms are *Euglena gracilis*; however, plant microorganisms used in the present invention are not limited to *Euglena gracilis*. Any plant microorganisms including algae may be used as long as they can fix carbon dioxide effectively through photosynthesis.

Further, in the above embodiments, the system of the present invention was all illustrated by taking the case where sunlight irradiates the system from right above. This does not limit the features of the present invention at all and can be easily realized by using reflecting mirrors capable of homing the sun and optical fibers which change the direction of sunlight irradiation. It goes without saying that, in such a case, the concepts of "above", "side", etc. are modified properly.

The shape of the culture bath, light-conducting plate, light-receiving means is not limited to that described in the above embodiments.

As is apparent from the description so far, a photosynthetic culture system of the present invention allows to avoid photosynthetic media like algae or plant microorganisms getting directly irradiated with intensive natural sunlight, which means a photosynthetic culture system of the present invention makes it possible to provide photosynthetic media with energy in a very effective manner.

A photosynthetic culture system of the present invention allows to conduct light to the whole volume of the culture bath without using mechanical energies such as circulation of fluid, diffusion and circulation of bubbles, which means a photosynthetic culture system of the present invention makes possible saving energy, saving area and saving volume, and consequently, highly increased volumetric efficiency of the culture system.

INDUSTRIAL APPLICABILITY

Thus, while man is faced with a difficulty of increasing carbon dioxide on a global scale, a photosynthetic culture system of the present invention provides improvements such as enhancement of carbon dioxide fixing ability of photosynthetic media, minimization of a photosynthetic culture system including light-conducting means, enhancement of efficiency, increase of controllability toward products of photosynthetic reaction; and consequently, a photosynthetic culture system of the present invention makes possible utilization of the technology of carbon dioxide fixation on a global scale which prevents global warming caused by industrial activities.

What is claimed is:

1. A photosynthetic culture system comprising:
    a culture bath holding a fluid containing plant microorganisms, and having a light receiving culture surface,
    a carbon dioxide supply for supplying carbon dioxide to the culture bath,
    a flat plate conductor disposed oppositely to the light receiving culture surface,
    a light receiver mounted above an edge of the flat plate conductor for conducting light to the flat plate conductor, and
    the flat plate conductor having a diffused reflection layer for reflecting the light diffusely and bending the light at substantially right angles to conduct the light substantially uniformly to the light receiving culture surface.

2. The photosynthetic culture system of claim 1 wherein the flat plate conductor has opposing surfaces, and the diffused reflection layer is disposed on one of the opposing surfaces, and
    another of the opposing surfaces has another diffused layer for diffusing the light.

3. The photosynthetic culture system of claim 1 wherein the diffused reflection layer includes small disks of translucent film, each disk having a predetermined diameter and a predetermined spacing from one another.

4. The photosynthetic culture system according to claim 1, wherein said light receiver has a light-converging portion and the area of the light entrance surface on top of the light-converging portion is larger than that of a bottom surface of the light-converging portion through which the light converges.

5. The photosynthetic culture system according to claim 1, wherein a side wall of said culture bath also serves as said flat plate conductor.

6. The photosynthetic culture system according to claim 1, wherein a top surface of said light receiver includes both top surfaces of said culture bath and said flat plate conductor and said light receiver is positioned on top of both said culture bath and said flat plate conductor.

7. The photosynthetic culture system according to claim 1, wherein a diffusing layer is provided on one surface of said flat plate conductor which is opposite to or in contact with said culture bath.

8. The photosynthetic culture system according to claim 7, wherein another diffused reflection layer is provided which reflects light diffusely on another surface of said flat plate conductor which is opposite to the one surface provided with said diffusing layer.

9. A collective photosynthetic culture system, wherein more than one photosynthetic culture system according to claim 1 are arranged so that the light-receiving culture surfaces of said culture baths will be in parallel to one another and the photosynthetic culture systems are connected to one another with a connecting pipe for supplying an fluid, a connecting pipe for transferring products, and a connecting pipe for supplying carbon dioxide.

10. The collective photosynthetic culture system according to claim 9, wherein more than one light receiver is carried by said photosynthetic culture system and said light receivers are integrally manufactured.

11. The collective photosynthetic culture system according to claim 10, wherein the light entrance surface of said integrally manufactured light receivers is flat.

12. The collective photosynthetic culture system according to claim 10, wherein said integrally manufactured light receivers has a thin protective film formed on a light entrance surface.

13. The collective photosynthetic culture system according to claim 9, wherein said flat plate conductor has a diffusing layer provided on both opposing surfaces of said flat plate conductor.

14. The collective photosynthetic culture system according to claim 9, wherein said flat plate conductor includes two side walls, which are opposite to each other, of said culture bath.

15. A collective photosynthetic culture system comprising:

a plurality of culture baths, each holding a fluid containing plant microorganisms, and each having a light receiving culture surface arranged parallel to one another, a plurality of flat plate conductors, each disposed oppositely to a respective light receiving culture surface, a plurality of light receivers formed integrally and mounted above the plurality of flat plate conductors, said plurality of light receivers having an integral flat top surface for receiving light, and an integral bottom surface configured as a plurality of convex surfaces for emitting the light, and each of the plurality of flat plate conductors receiving the light from a respective one of the convex surfaces and bending the light at substantially right angles to conduct the light substantially uniformly to a respective light receiving culture surface.

16. The culture system of claim 15 including a space formed between the integrally formed bottom surface and the flat plate conductors.

17. The culture system of claim 15 including the culture baths connected to one another by a pipe for supplying fluid and another pipe for supplying carbon dioxide.

18. A collective photosynthetic culture system comprising:

a plurality of culture baths, each holding a fluid containing plant microorganisms, and each having a light receiving culture surface arranged parallel to one another, a plurality of flat plate conductors, each sandwiched between light receiving culture surfaces of adjacent culture baths, a plurality of light receivers formed integrally and mounted above the plurality of flat plate conductors, each of the plurality of flat plate conductors receiving the light from a respective one of the plurality of light receivers and bending the light at substantially right angles to conduct the light to oppositely disposed light receiving culture surfaces, and each of the plurality of flat plate conductors having opposing surfaces, each opposing surface including a diffusing layer for substantially uniformly conducting the light to an opposing light receiving culture surface.

19. The culture system of claim 18 wherein the plurality of light receivers have an integral top surface configured as a plurality of convex surfaces for receiving light, and an integral bottom flat surface for emitting the light, and each of the plurality of flat plate conductors receiving the light from a respective one of the convex surfaces.

* * * * *

UNITED STATES PATENT AND TRADEMARK OFFICE
CERTIFICATE OF CORRECTION

PATENT NO. : 6,287,852 B1
DATED : September 11, 2001
INVENTOR(S) : Jiro Kondo et al.

It is certified that error appears in the above-identified patent and that said Letters Patent is hereby corrected as shown below:

<u>Title page,</u>
Item [73], Assignee, insert:

-- Jiro Kondo, Tokyo (JP)
  Yoshihisa Nakano, Osaka (JP)
  Kazutaka Miyatake, Osaka (JP)
  Nobuo Honami, Osaka (JP) --

Signed and Sealed this

Thirteenth Day of January, 2004

JON W. DUDAS
*Acting Director of the United States Patent and Trademark Office*